United States Patent
Heesch (10) Patent No.: US 9,399,104 B2
(45) Date of Patent: Jul. 26, 2016

(54) RESPIRATION SYSTEM FOR AN ANESTHESIA APPARATUS

(75) Inventor: Ralf Heesch, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 1042 days.

(21) Appl. No.: 13/495,409

(22) Filed: Jun. 13, 2012

(65) Prior Publication Data

US 2013/0000637 A1    Jan. 3, 2013

(30) Foreign Application Priority Data

Jul. 2, 2011   (DE) .................... 20 2011 102 764 U (51) Int. Cl.

| | |
|---|---|
| A61M 16/01 | (2006.01) |
| A61M 16/20 | (2006.01) |
| A61M 16/22 | (2006.01) |
| A61M 16/00 | (2006.01) |
| A61M 16/10 | (2006.01) |

(52) U.S. Cl.
CPC .......... *A61M 16/01* (2013.01); *A61M 16/0051* (2013.01); *A61M 16/0066* (2013.01); *A61M 16/0069* (2014.02); *A61M 16/1015* (2014.02); *A61M 16/104* (2013.01); *A61M 16/22* (2013.01); *A61M 2016/0027* (2013.01); *A61M 2016/0039* (2013.01)

(58) Field of Classification Search
CPC ............. A61M 2016/0027; A61M 2016/0039; A61M 16/0051; A61M 16/0066; A61M 16/0069; A61M 16/01; A61M 16/1005; A61M 16/1015; A61M 16/102; A61M 16/1025; A61M 16/103; A61M 16/1035; A61M 16/104; A61M 16/12; A61M 16/122; A61M 16/125; A61M 16/18; A61M 16/20; A61M 16/202; A61M 16/22; A61M 2202/02; A61M 2202/0208; A61M 2202/0241; A61M 2202/0266; A61M 2202/0283
See application file for complete search history.

(56) References Cited

U.S. PATENT DOCUMENTS

| | | | | |
|---|---|---|---|---|
| 3,378,005 | A | * | 4/1968 | Smith, Jr. ................ 128/205.13 |
| 5,320,093 | A | * | 6/1994 | Raemer .................... 128/203.12 |

(Continued)

FOREIGN PATENT DOCUMENTS

| | | |
|---|---|---|
| DE | 197 14 644 C2 | 9/1999 |
| DE | 199 04 119 A1 | 8/2000 |

(Continued)

*Primary Examiner* — Tan-Uyen (Jackie) T Ho
*Assistant Examiner* — Mark K Han
(74) *Attorney, Agent, or Firm* — McGlew and Tuttle, P.C.

(57) ABSTRACT

A respiration system includes a patient connection (1), an inspiratory branch (3), an expiratory branch (13), a rebreathing line (99), a reservoir (25), a $CO_2$ absorber (29), a radial compressor respiration drive (33), a fresh gas supply unit (51), an oxygen flushing device (55), connected to the rebreathing line, a pressure sensor (31) and an actuatable control valve (21), arranged in the rebreathing line between a second end (17) of the expiratory branch and the $CO_2$ absorber. The compressor, oxygen flushing device and fresh gas supply unit are arranged in the rebreathing line between the $CO_2$ absorber and a second end (7) of the inspiration branch. The compressor inlet points towards the $CO_2$ absorber and the outlet points towards the second end of the inspiratory branch. The pressure sensor is arranged in the rebreathing line between the compressor and the second end of the inspiratory branch.

20 Claims, 4 Drawing Sheets

(56) References Cited

U.S. PATENT DOCUMENTS

| | | | |
|---|---|---|---|
| 5,520,172 A | 5/1996 | Obermayer | |
| 5,568,910 A * | 10/1996 | Koehler et al. | 251/83 |
| 5,694,924 A * | 12/1997 | Cewers | 128/204.21 |
| 5,875,783 A * | 3/1999 | Kullik | 128/204.18 |
| 6,041,777 A * | 3/2000 | Faithfull et al. | 128/200.24 |
| 6,131,571 A * | 10/2000 | Lampotang et al. | 128/204.21 |
| 6,418,927 B1 * | 7/2002 | Kullik | 128/204.18 |
| 6,848,446 B2 * | 2/2005 | Noble | 128/207.18 |
| 7,438,072 B2 * | 10/2008 | Izuchukwu | 128/203.15 |
| 8,393,321 B2 * | 3/2013 | Burns et al. | 128/203.11 |
| 8,459,262 B2 * | 6/2013 | Ahlmen et al. | 128/205.13 |
| 8,539,950 B2 * | 9/2013 | Ahlmen et al. | 128/205.12 |
| 8,640,703 B2 * | 2/2014 | Broborg et al. | 128/205.14 |
| 2003/0233086 A1 * | 12/2003 | Burns et al. | 604/512 |
| 2004/0103899 A1 * | 6/2004 | Noble | 128/207.18 |
| 2006/0196505 A1 * | 9/2006 | Izuchukwu | 128/203.15 |
| 2009/0277448 A1 * | 11/2009 | Ahlmen et al. | 128/204.21 |

FOREIGN PATENT DOCUMENTS

| | | |
|---|---|---|
| DE | 199 58 532 C1 | 1/2001 |
| DE | 10 2006 032 498 B3 | 9/2007 |
| DE | 10 2007 019 487 B3 | 4/2008 |
| GB | 1 503 261 A | 3/1978 |

\* cited by examiner

RESPIRATION SYSTEM FOR AN ANESTHESIA APPARATUS

CROSS REFERENCE TO RELATED APPLICATIONS

This application claims the benefit of priority under 35 U.S.C. §119 of German Utility Model Application DE 20 2011 102 764.7 filed Jul. 2, 2011, the entire contents of which are incorporated herein by reference.

FIELD OF THE INVENTION

The present invention pertains to a respiration system (also known as a ventilation system) for an anesthesia apparatus with a patient connection, with an inspiratory branch, with an expiratory branch, with a rebreathing line, which connects the inspiratory branch to the expiratory branch, with a fresh gas supply unit, with an oxygen flushing means and with a radial compressor as a respiration drive, which is arranged in the rebreathing line.

BACKGROUND OF THE INVENTION

Anesthesia devices with an inspiratory branch and an expiratory branch are shown in the state of the art. So-called half-closed anesthesia systems are used for reusing the portion of anesthesia gas in the expired gas. Such a half-closed anesthesia system is shown in U.S. Pat. No. 5,520,172 A. So-called fully closed respiration systems are used in order to further reduce the amount of anesthesia that must be conveyed unused into the half-closed anesthesia circulation. Besides the closed circuit, an array of valves are used for feeding fresh gas and inhalants into the breathing circuit and controlled such that the loss of anesthesia gas is as low as possible.

DE 10 2006 032 498 B3 shows a respiration or anesthesia and therapy device for patients which has a controllable valve in the expiration branch to keep the loss of anesthesia gas as low as possible.

A respirator with a breathing circuit is described in DE 199 58 532 C1. In this breathing circuit, defined breathing gas volumes are fed to the patient and the current operating state is reliably monitored. A rotary compressor as a gas-feeding element, a reversible breathing gas reservoir, gas volume flow sensors, nonreturn valves, a controllable stop valve and an associated measuring and regulating unit are present as elements in the respirator.

DE 197 14 644 C2 shows a gas feeding means for a respiration and anesthesia device. The gas feeding means for a respiration and anesthesia device is designed in the form of a radial compressor with backwards curved blades. A compressor wheel, which feeds a quantity of air from a gas inlet to a gas outlet, is arranged rotatably in a fixed housing. The compressor wheel is driven via an electric motor.

A closed respiration system, which has, starting from a patient connection or from a Y-piece, an inspiratory branch and an expiratory branch, which are in turn connected to one another via a rebreathing line within the system, so that gas expired by the patient can be returned to the inspiratory branch, while it flows, among other things, through a $CO_2$ absorber and gas components absorbed by the patient are replaced by means of a fresh gas supply unit, is already known from the instructions for use of the respiration system of the "Zeus Infinity Empowered" respiration system of Dräger Medical GmbH.

It is necessary in such closed respiration systems for the entire breathing circuit comprising the inspiratory branch, expiratory branch and rebreathing line, to be able to be flushed with oxygen as quickly as possible in order to abruptly increase the oxygen concentration in the breathing gas, which is fed to the patient.

This is achieved in the system described in the instructions for use mentioned in the introduction by maintaining, on the one hand, a constant breathing gas flow in the respiration system of the anesthesia apparatus and in the entire breathing circuit up to the Y-piece leading to the patient by means of the respiration drive designed as a radial compressor and, on the other hand, by being able to admit oxygen into the breathing circuit by means of an oxygen flushing means arranged between the expiratory branch and the $CO_2$ absorber.

Such an oxygen flushing means is known as an "$O_2$ flush" and is intended typically for anesthesia apparatuses as an operational control accessible to the user in this form. The oxygen flushing means has an oxygen port for this, for example, as a port to an oxygen tank that is under pressure or to a pressurized oxygen line.

Furthermore, a means is present, with which an oxygen volume flow can be set and dispensed when actuating the flushing means. Based on the constant flow, the oxygen that may be optionally admitted is then distributed in the entire breathing circuit.

However, such a system is associated with the drawback that a gas flow must be continuously maintained in the breathing circuit in order to ensure that the oxygen is also distributed in the entire breathing circuit, and it does not happen that parts thereof are not flushed. If the latter happened, a so-called rebound effect could occur, during which breathing gas with a low oxygen concentration is again fed after a short time, during which breathing gas with high oxygen concentration was admitted to the patient after actuation of the oxygen flushing means.

Another problem in closed respiration systems is that it is desirable, on the one hand, to provide a constant fresh gas flow from the fresh gas supply unit, which flow is now flowing through an anesthetic evaporator, so that this constant flow can be used in the evaporator to absorb the anesthetic.

The general mode of operation of an anesthetic evaporator is known from GB 1 503 261.

Such an evaporator cannot be operated reliably if the intensity of the flow varies as a result and if a pulsed flow is used. However, the advantage of anesthetic evaporators is that these make do without complicated electrical components and operate very reliably if flow passing through them is continuous.

However, an electric injection pump, which injects anesthetic into the pulsed fresh gas flow, is used instead of an anesthetic evaporator in the respiration system explained above, which is described in the instructions for use. This complicates the system described further.

SUMMARY OF THE INVENTION

An object of the present invention is therefore to provide a respiration system for an anesthesia apparatus, which is controlled in a less complicated manner and makes possible rapid flushing of the entire breathing circuit with oxygen.

According to the invention a respiration system is provided that comprises:
 a patient connection;
 an inspiratory branch, which has a first end and a second end as well as a nonreturn valve, which opens when the pressure on the side of the nonreturn valve pointing towards the second end is above that on the side of the nonreturn valve pointing towards the first end, the first end being connected to the patient connection;

an expiratory branch, which has a first end and a second end as well as a nonreturn valve, which opens when the pressure on the side of the nonreturn valve pointing towards the first end is above that on the side of the nonreturn valve pointing towards the second end, the first end being connected to the patient connection;

a rebreathing line, which connects the second end of the inspiratory branch to the second end of the expiratory branch;

a reservoir, which is connected to the rebreathing line and is preferably designed as a manual breathing bag;

a $CO_2$ absorber arranged in the rebreathing line for absorbing $CO_2$ contained in the breathing gas;

a radial compressor arranged in the rebreathing line between the $CO_2$ absorber and the second end of the inspiratory branch as a respiration drive, which has a housing, in which a fan wheel is mounted in such a way that it driven rotating in one direction of rotation about an axis of rotation, wherein said fan wheel has blades, which extend in the direction of the axis of rotation and which extend away from the axis of rotation towards the outside, wherein said blades are preferably curved against the direction of rotation in relation to radial lines originating from the axis of rotation and wherein the housing has an inlet pointing away from the fan wheel in the area of the axis of rotation in the direction of said axis of rotation and an outlet in the plane of the fan wheel in the area of the circumference of said fan wheel;

a fresh gas supply unit, which is connected to the rebreathing line, an oxygen flushing means, which is connected to said rebreathing line and is designed to admit oxygen into the rebreathing line;

a pressure sensor, which is arranged in the rebreathing line between the $CO_2$ absorber and the second end of the inspiratory branch; and an actuatable control valve, which is arranged in the rebreathing line between the second end of the expiratory branch and the $CO_2$ absorber.

The radial compressor, oxygen flushing means and fresh gas supply unit are arranged between the $CO_2$ absorber and the second end of the inspiratory branch in the rebreathing line. The inlet points towards the $CO_2$ absorber and the outlet points towards the second end of the inspiratory branch. The pressure sensor is arranged between the radial compressor and the second end of the inspiratory branch in the rebreathing line.

The design according to the present invention, in which the oxygen flushing means is arranged in the rebreathing line such that it is provided either on the side of the radial compressor facing away from the inspiratory branch or on the side of the radial compressor facing this the inspiratory branch, makes it possible for the oxygen fed by the oxygen flushing means to flow through the radial compressor and/or directly into the inspiratory branch and hence to the patient. However, the oxygen may also flow towards the $CO_2$ absorber and further to the nonreturn valve of the expiratory branch. The fact is utilized according to the invention that it is possible in a radial compressor for gas to also flow through the compressor against the pressure rise generated by the compressor from the outlet to the inlet, because a radial compressor has no valves, but only generates a constant pressure rise that is essentially independent from the volume flow during its operation.

It is made possible, on the whole, in the design according to the present invention to flush the entire breathing circuit with oxygen without a complicated control being necessary herefor. This is carried out in a parallel manner, in which the oxygen flows through and flushes quasi simultaneously the components present in the anesthesia apparatus in the respiration circuit as well as the connection to the patient with the inspiratory branch, with the Y-piece and with the expiratory branch.

Furthermore, it is made possible by the pressure sensor being arranged between the radial compressor and the second end of the inspiratory branch to regulate the pressure on the side of the nonreturn valve facing away from the patient connection in the inspiratory branch by means of the radial compressor or the speed of rotation thereof such that the pressure difference between the two sides of the nonreturn valve in the inspiratory branch is only slightly below the threshold at which the nonreturn valve opens, so that the vacuum, which must then be generated by a patient for spontaneous breathing is only low. Nevertheless, it is possible for a constant fresh gas feed to take place from the fresh gas supply unit without this already pushing up the nonreturn valve in the inspiratory branch, because the threshold of the nonreturn valve is selected to be just such that the fresh gas feed is not sufficient for this.

According to a preferred exemplary embodiment, the radial compressor is arranged in the rebreathing line between the $CO_2$ absorber on one side of the radial compressor and the fresh gas supply unit and the oxygen flushing means on the other side of the radial compressor. This means that the oxygen flushing means is close to the inspiratory branch and hence close to the patient, so that oxygen reaches the patient very rapidly when the flushing means is actuated. Conversely, the oxygen fed can nevertheless flow back to the $CO_2$ absorber through the radial compressor and further in the direction of the expiratory branch into the rebreathing line and likewise fill this with oxygen in case of a flushing operation.

Even though the oxygen flushing means is thus located close to the inspiratory branch, it is nevertheless avoided that parts of the rebreathing line are not flushed with oxygen, as a result of which the above-mentioned rebound effect would occur, in which case breathing gas with reduced oxygen concentration would again reach the patient shortly after flushing.

According to another preferred embodiment, the radial compressor is arranged between the $CO_2$ absorber and the oxygen flushing means on one side of the radial compressor and the fresh gas supply unit on the other side. The pressure in front of the nonreturn valve can be regulated in this case in the inspiratory branch in case of a preset fresh gas flow by means of the radial compressor. This simplifies the use of an anesthetic evaporator, through which there is a constant flow, in the feed line between the fresh gas supply unit and the rebreathing line.

On the other hand, the flow of oxygen into the area of the rebreathing line, which extends between the radial compressor and the expiratory branch, is facilitated by the oxygen flushing means being arranged between the $CO_2$ absorber and the radial compressor.

Finally, the fresh gas supply unit preferably has an anesthetic evaporator, through which the fresh gas fed in flows. Such anesthetic evaporators have the property of making do without complicated regulating mechanisms.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
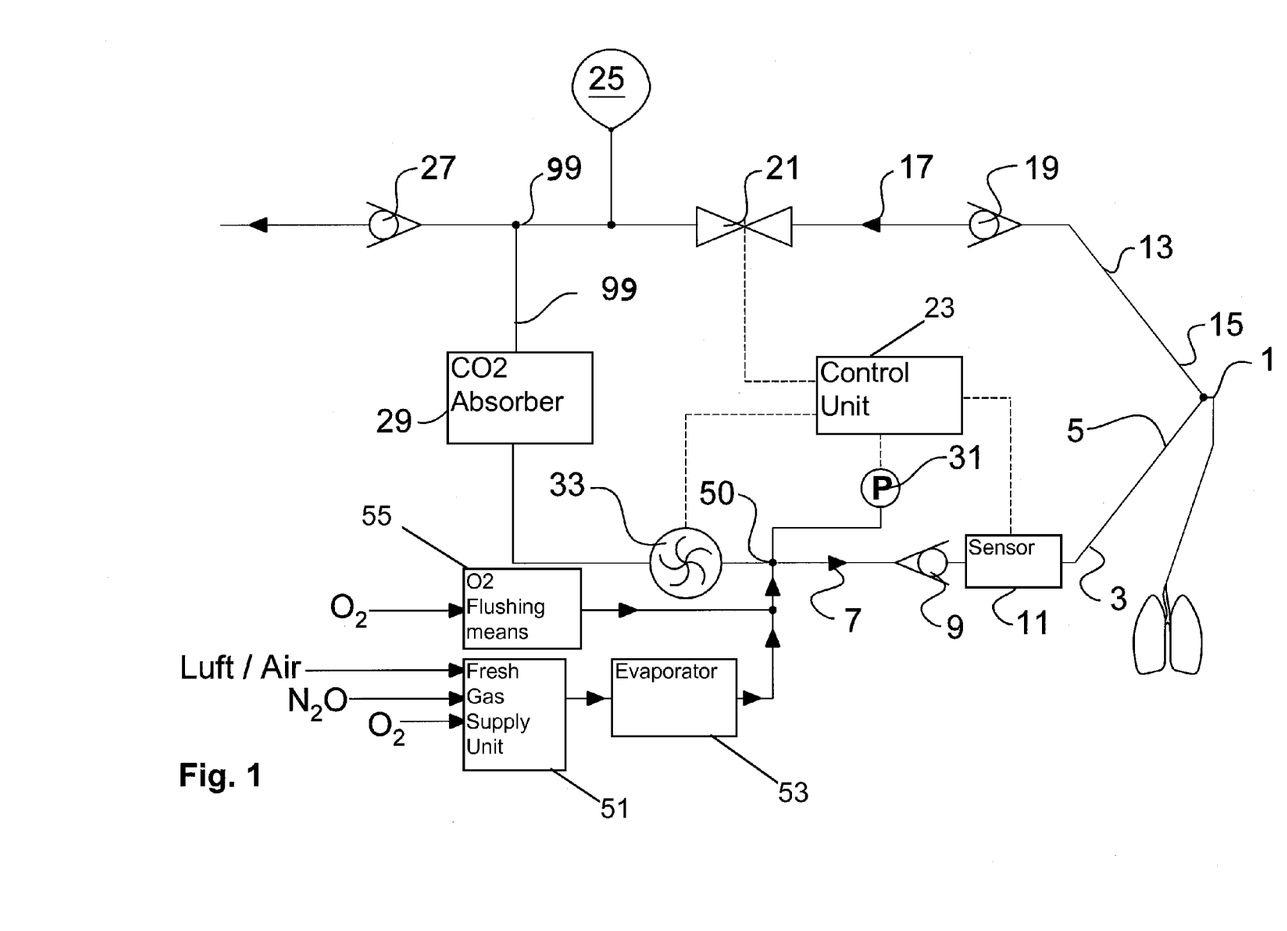
FIG. 1 is a schematic view of a first exemplary embodiment of a respiration system according to the present invention.

Referring to the drawings in particular, the first exemplary embodiment of a respiration system, which is shown in FIG. 1, has a patient connection 1, which is designed as a Y-piece and from which an inspiratory branch 3 extends, which has a first end 5, which is arranged adjacent to the patient connection 1, and a second end 7, which is located away from the patient connection 1. In addition, a nonreturn valve 9, which is designed such that it opens when the pressure on the side of the nonreturn valve 9 facing the second end 7 is higher than the pressure on the side pointing towards the first end 5, is provided in the inspiratory branch 3. In particular, nonreturn valve 9 is designed such that it opens only when the difference between the pressure on the side pointing towards the second end 7 and that on the side pointing towards the first end 5 is above a preset threshold. It is ensured by this design that gas expired by the patient and discharged from the patient connection 1 cannot flow out of the inspiratory branch 3 during an expiration phase. Finally, the inspiratory branch 3 also has a volume flow sensor 11, with which the volume flow can be measured in the inspiratory branch 3.

Besides the inspiratory branch 3, an expiratory branch 13, which has a first end 15 arranged adjacent to the patient connection 1 and a second end 17 located away from the first end 15 and which extends in-between, extends from the patient connection 1 as well. In addition, a nonreturn valve 9 is likewise provided in the expiratory branch 13, but this nonreturn valve 9 is arranged and designed such that it opens only if the pressure on the side of the nonreturn valve 9 facing the first end 15 is above the pressure that prevails on the side of the nonreturn valve 9 facing the second end 17. No breathing gas can thus flow from the second end 17 in the direction of the patient connection 1.

A rebreathing line 99, which connects the second ends 7, 17 to one another, extends between the second end 7 of the inspiratory branch 3 and the second end 17 of the expiratory branch 13, wherein said rebreathing line 99 may be arranged in a housing of the system. Viewed from the second end 17 of the expiratory branch, a controllable valve 21, which can be actuated electrically and is connected to a control unit 23 likewise provided in the respiration system and can be actuated by said control unit 23, is arranged first in the rebreathing line 99. Controllable valve 21 is followed by a reservoir likewise connected to the rebreathing line 99 in the form of a manual breathing bag 25, which has a variable volume and in which gas expired by the patient and gas being discharged from the expiratory branch 13 can be taken up. Viewed from the second end 17 of the expiratory branch 13, an anesthetic gas escape valve 27 is arranged behind the manual breathing bag 25, said anesthetic gas escape valve 27 having a preset threshold pressure, which must be given in the rebreathing line 99 in order for the anesthetic gas escape valve 27 to open.

It is ensured hereby that no excessively high pressure can build up in the rebreathing line 99 when the manual breathing bag 25 is fully opened. The anesthetic gas escape valve 27 is joined in the rebreathing line 99 by a $CO_2$ absorber 29, which is intended to absorb $CO_2$ present in the breathing gas.

As can be seen below, a pressure sensor 31, which is likewise connected to the control unit 23, is connected to the rebreathing line 99 between the $CO_2$ absorber and the second end 7 of the inspiratory branch 3, adjacent to the second end 7, so that the pressure in the rebreathing line 99 can be detected in the area of the second end 7 of inspiratory branch 3.

Figure 3:
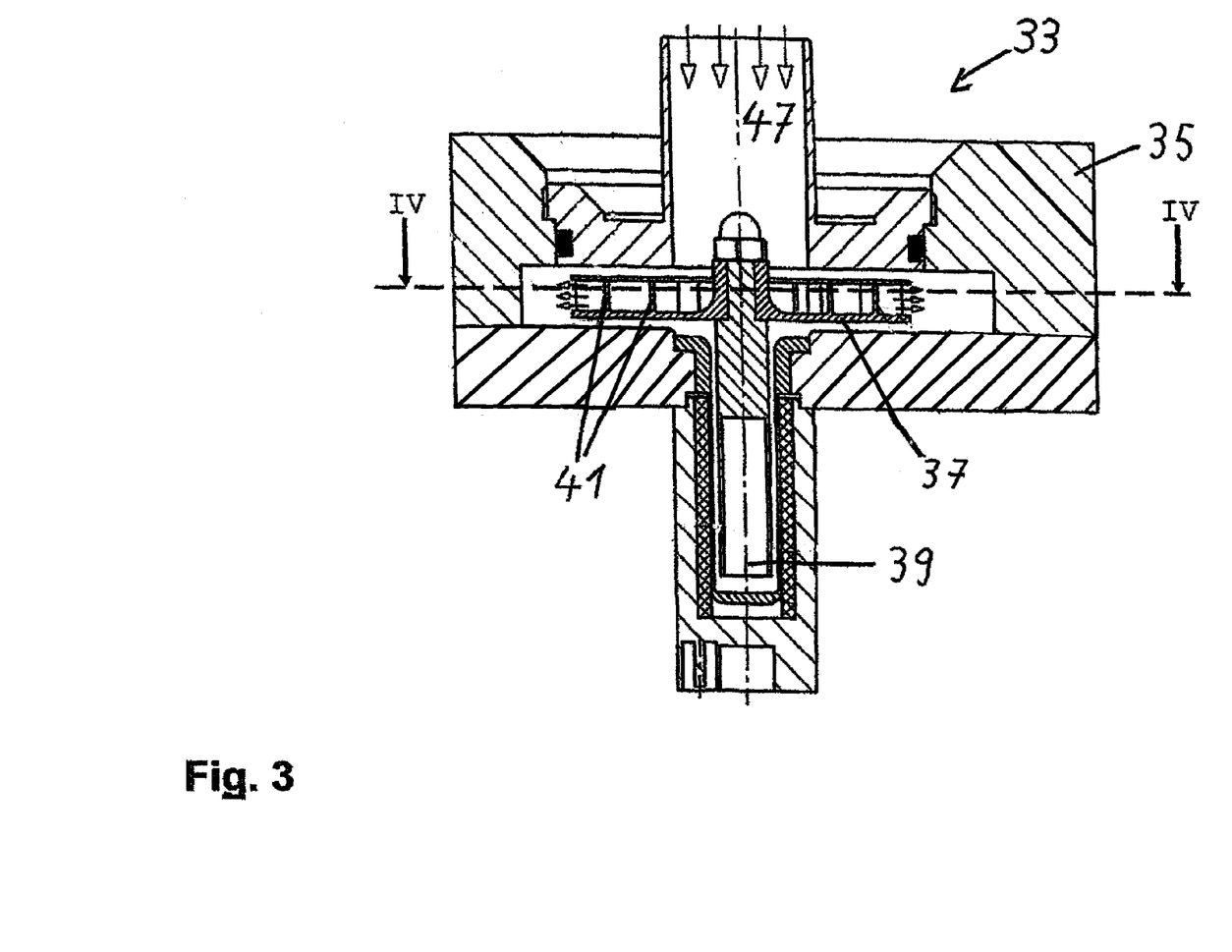
FIG. 3 is a cross section through a radial compressor, which is used in the exemplary embodiments shown in FIGS. 1 and 2.
Figure 4:
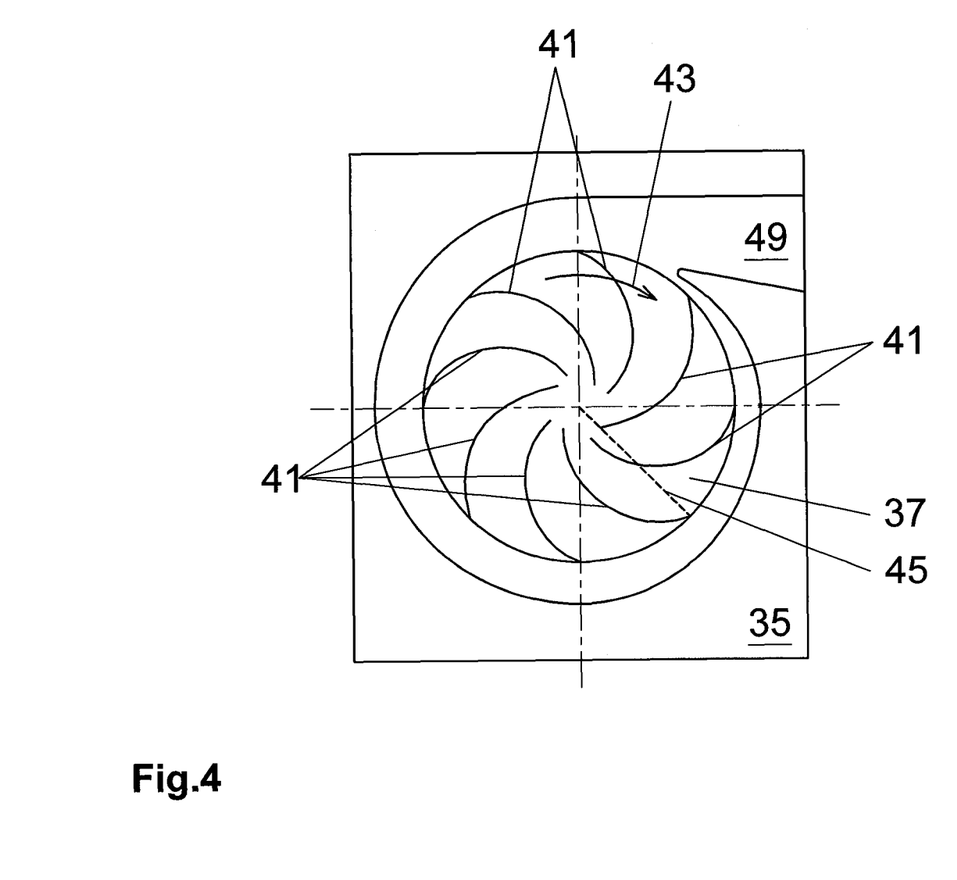
FIG. 4 is a sectional view along line IV-IV from FIG. 3.

A radial compressor 33, whose design is shown in FIGS. 3 and 4, is provided in the rebreathing line 99 between pressure sensor 31 and $CO_2$ absorber. Radial compressor 33 has a housing 35, in which a fan wheel 37 is mounted such that it is rotatable about an axis of rotation 39. Fan wheel 37 has blades 41 extending in the direction of the axis of rotation 39, i.e., the blades 41 are of a strip-shaped design, and their transverse direction extends in parallel to the axis of rotation 39. As can also be seen from FIG. 4, the blades 41 extend away from the axis of rotation 39 to the outside. Fan wheel 37 is driven rotatably about the axis of rotation 39 in a direction of rotation 43, and it can be seen from FIG. 4 that the blades 41 are shaped such that they are curved against the direction of rotation 43 in relation to radial lines 45 originating from the axis of rotation 39, i.e., the distance between blades 41 and radial line 45 progressively increases with increasing distance from the axis of rotation 39. Finally, housing 35 has an inlet 47 pointing in the direction of the axis of rotation 39 and an outlet 49 arranged in the plane of fan wheel 37. The radial compressor 33 is arranged in the rebreathing line 99 such that inlet 47 points towards the $CO_2$ absorber, while outlet 49 points in the direction of the second end 7 of the inspiratory branch 3, so that the radial compressor 33 generates a flow from the $CO_2$ absorber 29 to the inspiratory branch 3 during the operation.

When the fan wheel 37 is driven rotatingly in the direction of rotation 43, air entering through inlet 47 is pressurized in the direction of the outlet 49, and the pressure difference generated by radial compressor 33 between inlet 47 and outlet 49 is essentially independent from the volume flow being delivered by compressor 33 and depends essentially only on the speed of rotation. Furthermore, it is possible for gas to also flow from outlet 49 to inlet 47, even if the fan wheel 37 is being driven rotatingly, because the radial compressor has no valve hindering such a direction of flow.

As can also be seen from FIG. 1, a first port 50, which is located in this case at the point where the pressure sensor 31 is also connected to the rebreathing line 99 and via which a fresh gas supply unit 51, which has an anesthetic evaporator 53, is connected to the rebreathing line 99, is also provided between the $CO_2$ absorber 29 and the pressure sensor 31, besides the radial compressor 33. In addition, an oxygen flushing means 55 is connected to the rebreathing line 99 via the same first port 50. The oxygen flushing means 55 is connected in the example being shown here to a pressurized oxygen source and has means with which oxygen can be introduced into the rebreathing line 99 at a preset volume flow when the oxygen flushing means is actuated.

Thus, the radial compressor 33, oxygen flushing means 55 and fresh gas supply unit 51 are arranged in this exemplary embodiment between the $CO_2$ absorber 29 and second end 7 of the inspiratory branch 3 in the rebreathing line 99, with inlet 47 pointing towards the CO$_2$ absorber 29 and outlet 49 pointing towards the second end 7 of the inspiratory branch 3. In addition, the pressure sensor 31 is arranged in the rebreathing line 99 between the radial compressor 33 and second end 7 of the inspiratory branch 3. Finally, the radial compressor 33 is arranged in this preferred exemplary embodiment in the rebreathing line 99 between the CO$_2$ absorber on one side of the radial compressor 33 and the fresh gas supply unit 51 and oxygen flushing means 55 on the other side of the radial compressor 33.

The respiration system shown in FIG. 1 operates as follows during normal operation. The controllable valve 21 is first closed by the control unit 23, and breathing gas is delivered by the radial compressor 33 from the manual breathing bag 25 through the CO$_2$ absorber 29 into the inspiratory branch 3 to the patient connection 1, and a preset fresh gas flow, which flows through the anesthetic evaporator 53, also flows, besides, from the fresh gas supply unit 51 into the rebreathing line 99 and then enters the inspiratory branch 3.

The controllable valve 21 opens after the end of the inspiration phase, and gas flows from the patient connection 1 through the expiratory branch 13 back into the manual breathing bag 25, which acts as a reservoir in this case. While the control valve 21 is open, radial compressor 33 is stopped or operated at a reduced speed of rotation, so that the pressure generated at pressure sensor 31 by radial compressor 33 and fresh gas supply unit 51 is not sufficient to open the nonreturn valve 9.

When it is necessary to increase the oxygen concentration in the breathing gas, the oxygen flushing means 55 is actuated, and oxygen flows into rebreathing line 99. The flow of oxygen is now selected to be such that the pressure occurring at the nonreturn valve 9 of the inspiratory branch 3 is so high that this valve opens and oxygen flows into the inspiratory branch 3. In addition, due to the radial compressor 33, which also permits a flow opposite the direction of delivery proper of the radial compressor 33, oxygen can flow from the oxygen flushing means 55 through the rebreathing line 99 to the CO$_2$ absorber 29, past the anesthetic escape valve 27 to the manual breathing bag 25 and further to the nonreturn valve 19. Oxygen can thus reach both the patient connection 1 and the complete rebreathing line 99 despite the existing respiration drive in the form of the radial compressor 33, without it being necessary to provide a permanent flow through the inspiratory branch 3, expiratory branch 13 and rebreathing line 99.

In addition, the above-described respiration system makes it possible to provide a constant fresh gas flow from the fresh gas supply unit 51, which flows continuously through the anesthetic evaporator 53 and the manual breathing bag 25 is thus filled up with fresh gas via the rebreathing line 99 and CO$_2$ absorber 29, and fresh gas also reaches the patient via the inspiratory branch 3 with the cooperation of the radial compressor 33.

This makes it possible to use such an evaporator and avoids the need to use complicated injection pumps combined with a complicated control and regulation. By controlling the speed of rotation of the radial compressor 33 by means of the pressure sensor 31 and control unit 23, the pressure can now be controlled in the area of the second end 7 of the inspiratory branch 3 even in case of a constant fresh gas flow such that the pressure difference between the two sides of the nonreturn valve 9 in the inspiratory branch 3 is below the threshold at which the nonreturn valve 9 opens by a predetermined amount.

On the whole, it is achieved in the above-described respiration system that the entire breathing circuit can be flushed with oxygen without a complicated control being required for this.

Figure 2:
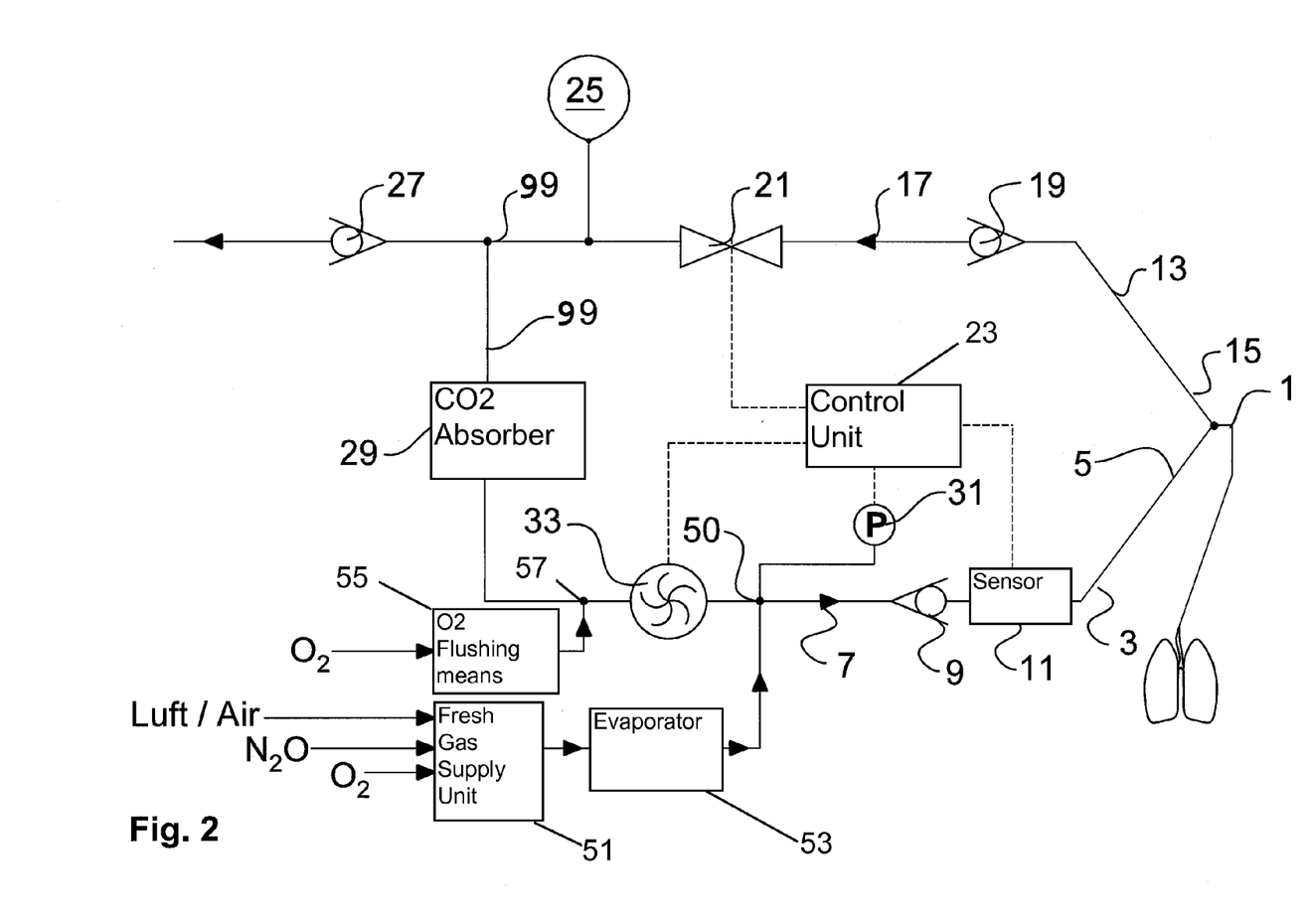
FIG. 2 is a schematic view of a second preferred exemplary embodiment of a system according to the present invention.

The second exemplary embodiment shown in FIG. 2 differs from the first exemplary embodiment shown in FIG. 1 only in that the oxygen flushing means 55 is connected to a second port 57 on the side of the radial compressor 33 pointing towards the CO$_2$ absorber between the CO$_2$ absorber 29 and the radial compressor 33 in the rebreathing line 99.

Identical components in FIGS. 1 and 2 are designated by the same reference numbers. However, the mode of operation of the second exemplary embodiment according to this FIG. 2 does not differ from the mode of operation of the first embodiment according to FIG. 1.

It is also possible in such an arrangement for oxygen flowing into the rebreathing line 99 from the oxygen flushing means 55 to flow both into the inspiratory branch 3 and through the CO$_2$ absorber 29 into the manual breathing bag 25 and into control valve 21 up to the second end 17 of the expiratory branch 13 and to the nonreturn valve 9 arranged thereon.

While specific embodiments of the invention have been shown and described in detail to illustrate the application of the principles of the invention, it will be understood that the invention may be embodied otherwise without departing from such principles.

APPENDIX

List of Reference Numbers

1 Patient connection
3 Inspiratory branch
5 First end (inspiratory branch)
7 Second end (inspiratory branch)
9 Nonreturn valve (inspiratory branch)
11 Volume flow sensor
13 Expiratory branch
15 First end (expiratory branch)
17 Second end (expiratory branch)
21 Controllable valve
23 Control unit
25 Manual breathing bag (reservoir)
27 Anesthetic escape valve
29 CO$_2$ absorber
31 Pressure sensor
33 Radial compressor
35 Housing
37 Fan wheel
39 Axis of rotation
41 Blade
43 Direction of rotation
45 Radial line
47 Inlet
49 Outlet
50 First port
51 Fresh gas supply unit
53 Anesthetic evaporator
55 Oxygen flushing means
57 Second port
99 Rebreathing Line
19 Nonreturn valve (expiratory branch)

What is claimed is:

1. A respiration system for an anesthesia apparatus, the respiration system comprising:
a patient connection;
an inspiratory branch, which has an inspiratory branch first end and an inspiratory branch second end as well as an inspiratory branch nonreturn valve which opens when pressure on a side of the inspiratory branch nonreturn valve pointing towards said inspiratory branch second end is above pressure on a side of said inspiratory branch nonreturn valve pointing towards said inspiratory branch first end, wherein said inspiratory branch first end is connected to said patient connection;

an expiratory branch, which has an expiratory branch first end and an expiratory branch second end as well as an expiratory branch nonreturn valve which opens when pressure on a side of said expiratory branch nonreturn valve pointing towards said expiratory branch first end is above pressure on a side of said expiratory branch nonreturn valve pointing towards said expiratory branch second end, wherein said expiratory branch first end is connected to said patient connection;

a rebreathing line, which connects said inspiratory branch second end to said expiratory branch second end;

a reservoir connected to said rebreathing line;

a $CO_2$ absorber arranged in said rebreathing line for absorbing $CO_2$ contained in the breathing gas;

a radial compressor arranged in said rebreathing line between said $CO_2$ absorber and said inspiratory branch second end as a respiration drive, said radial compressor comprising a fan wheel mounted in a housing and rotatingly driven in a direction of rotation about an axis of rotation, wherein said fan wheel has blades extending in a direction of the axis of rotation and extending outwardly away from said axis of rotation and wherein said housing has an inlet pointing away from said fan wheel in an area of said axis of rotation in a direction of said axis of rotation and an outlet arranged in a plane of said fan wheel in an area of a circumference of said fan wheel;

a fresh gas supply unit connected to said rebreathing line;

an oxygen flushing means, connected to said rebreathing line, for introducing oxygen into said rebreathing line;

a pressure sensor arranged between said $CO_2$ absorber and said inspiratory branch second end; and an actuatable control valve arranged in said rebreathing line between said expiratory branch second end and said $CO_2$ absorber, wherein:

said radial compressor, said oxygen flushing means and said fresh gas supply unit have an operative connection in said rebreathing line between said $CO_2$ absorber and said inspiratory branch second end;

said inlet points towards said $CO_2$ absorber;

said outlet points towards said inspiratory branch second end; and said pressure sensor is arranged in said rebreathing line between said radial compressor and said inspiratory branch second end.

2. A respiration system in accordance with claim 1, wherein said radial compressor is arranged in said rebreathing line between said $CO_2$ absorber on one side of said radial compressor and said fresh gas supply unit and said oxygen flushing means on another side of said radial compressor.

3. A respiration system in accordance with claim 1, wherein said radial compressor is arranged in said rebreathing line between said $CO_2$ absorber and said oxygen flushing means on one side of said radial compressor and said fresh gas supply unit on another side of said radial compressor.

4. A respiration system in accordance with claim 1, wherein said fresh gas supply unit has an anesthetic evaporation means, through which fresh gas flows.

5. A respiration system in accordance with claim 1, wherein fresh gas is delivered to said rebreathing line at a fresh gas delivery position via said fresh gas supply unit and the oxygen is delivered to said rebreathing line at an oxygen delivery position via said oxygen flushing means, said fresh gas delivery position and said oxygen delivery position being located downstream of said carbon dioxide absorber and upstream of said inspiratory branch nonreturn valve with respect to a flow of fluid in said rebreathing line.

6. A respiration system for an anesthesia apparatus, the respiration system comprising:

a patient connection;

an inspiratory branch with an inspiratory branch first end and an inspiratory branch second end, said inspiratory branch first end being connected to said patient connection;

an inspiratory branch nonreturn valve between said inspiratory branch first end and said inspiratory branch second end for opening when pressure on an inspiratory branch second end side of said inspiratory branch nonreturn valve is above pressure on an inspiratory branch first end side of said inspiratory branch nonreturn valve;

an expiratory branch with an expiratory branch first end and an expiratory branch second end, said expiratory branch first end being connected to said patient connection;

an expiratory branch nonreturn valve between said expiratory branch first end and said expiratory branch second end for opening when pressure on an expiratory branch first end side of said expiratory branch nonreturn valve is above pressure on an expiratory branch second end side of said expiratory branch nonreturn valve;

a rebreathing line connected to said inspiratory branch second end and to said expiratory branch second end;

a reservoir connected to said rebreathing line;

a $CO_2$ absorber arranged in said rebreathing line for absorbing $CO_2$ contained in the breathing gas;

a radial compressor arranged in said rebreathing line between said $CO_2$ absorber and said inspiratory branch second end as a respiration drive, said radial compressor comprising a fan wheel mounted in a housing and rotatingly driven in a direction of rotation about an axis of rotation, wherein said fan wheel has blades extending in a direction of the axis of rotation and extending outwardly away from said axis of rotation and wherein said housing has an inlet pointing away from said fan wheel in an area of said axis of rotation in a direction of said axis of rotation and an outlet arranged in a plane of said fan wheel in an area of a circumference of said fan wheel;

a fresh gas supply unit connected to said rebreathing line;

an oxygen flushing means, connected to said rebreathing line, for introducing oxygen into said rebreathing line;

a pressure sensor arranged between said $CO_2$ absorber and said inspiratory branch second end; and an actuatable control valve arranged in said rebreathing line between said expiratory branch second end and said $CO_2$ absorber, wherein:

said radial compressor, said oxygen flushing means and said fresh gas supply unit are connected to said rebreathing line between said $CO_2$ absorber and said inspiratory branch second end;

said inlet is on a $CO_2$ absorber side of said radial compressor;

said outlet is on an inspiratory branch second end side of said radial compressor; and said pressure sensor is arranged in said rebreathing line between said radial compressor and said inspiratory branch second end.

7. A respiration system in accordance with claim 6, wherein said radial compressor is connected to said rebreathing line with said $CO_2$ absorber and said fresh gas supply unit on one side and said oxygen flushing means on another side of said radial compressor.

8. A respiration system in accordance with claim 7, wherein said fresh gas supply unit has an anesthetic evaporation means, through which fresh gas flows.

9. A respiration system in accordance with claim 6, wherein said radial compressor is arranged in said rebreathing line with said $CO_2$ absorber and said oxygen flushing means on one side of said radial compressor and said fresh gas supply unit on another side of said radial compressor.

10. A respiration system in accordance with claim 7, wherein said fresh gas supply unit has an anesthetic evaporation means, through which fresh gas flows.

11. A respiration system in accordance with claim 6, wherein said fresh gas supply unit has an anesthetic evaporation means, through which fresh gas flows.

12. A respiration system in accordance with claim 6, wherein fresh gas is delivered to said rebreathing line at a fresh gas delivery position via said fresh gas supply unit and the oxygen is delivered to said rebreathing line at an oxygen delivery position via said oxygen flushing means, said fresh gas delivery position and said oxygen delivery position being located downstream of said carbon dioxide absorber and upstream of said inspiratory branch nonreturn valve with respect to a flow of fluid in said rebreathing line.

13. A respiration system for an anesthesia apparatus, the respiration system comprising:
a breathing circuit comprising an inspiratory branch, an expiratory branch and a rebreathing line connected to said inspiratory branch and connected to said expiratory branch;
a patient connection comprising a Y connection to said inspiratory branch and to said expiratory branch;
an inspiratory branch nonreturn valve operatively connected to said inspiratory branch adjacent to said rebreathing line for opening when pressure in said inspiratory branch is higher on a rebreathing line side of said inspiratory branch nonreturn valve than on a patient connection side of said inspiratory branch nonreturn valve;
an expiratory branch nonreturn valve operatively connected to said expiratory branch adjacent to said rebreathing line for opening when pressure in said expiratory branch is higher on a patient connection side of said inspiratory branch nonreturn valve than on a rebreathing line side of said inspiratory branch nonreturn valve;
a reservoir connected to said rebreathing line;
a $CO_2$ absorber operatively connected to said rebreathing line for absorbing $CO_2$ contained in breathing gas flowing through said rebreathing line;
a radial compressor operatively connected to said rebreathing line between said $CO_2$ absorber and said inspiratory branch nonreturn valve, said radial compressor comprising a fan wheel mounted in a housing and rotatingly driven in a direction of rotation about an axis of rotation, wherein said fan wheel has blades extending in a direction of the axis of rotation and extending outwardly away from said axis of rotation and wherein said housing has an inlet pointing away from said fan wheel in an area of said axis of rotation in a direction of said axis of rotation and an outlet arranged in a plane of said fan wheel in an area of a circumference of said fan wheel;
a fresh gas supply unit connected to said rebreathing line;
an oxygen flushing source connected to said rebreathing line for introducing oxygen into said rebreathing line;
a pressure sensor operatively connected to said rebreathing line between said $CO_2$ absorber and said inspiratory branch nonreturn valve; and
an actuatable control valve operatively connected to said rebreathing line between said expiratory branch nonreturn valve and said $CO_2$ absorber, wherein:
said radial compressor, said oxygen flushing source and said fresh gas supply unit are operatively connected to said rebreathing line between said $CO_2$ absorber and said inspiratory branch nonreturn valve;
said inlet of said radial compressor is on a $CO_2$ absorber side of said radial compressor;
said outlet of said radial compressor is on an inspiratory branch nonreturn valve side of said radial compressor; and
said pressure sensor is operatively connected to said rebreathing line between said radial compressor and said inspiratory branch nonreturn valve.

14. A respiration system in accordance with claim 13, wherein said radial compressor is connected to said rebreathing line with said $CO_2$ absorber and said fresh gas supply unit connected to said rebreathing line on one side of said radial compressor and said oxygen flushing source connected to said rebreathing line on another side of said radial compressor.

15. A respiration system in accordance with claim 14, wherein said fresh gas supply unit comprises an anesthetic evaporator through which fresh gas flows.

16. A respiration system in accordance with claim 13, wherein said radial compressor is arranged in said rebreathing line with said $CO_2$ absorber and said oxygen flushing source connected to said rebreathing line on one side of said radial compressor and said fresh gas supply unit connected to said rebreathing line on another side of said radial compressor.

17. A respiration system in accordance with claim 16, wherein said fresh gas supply unit comprises an anesthetic evaporator through which fresh gas flows.

18. A respiration system in accordance with claim 13, wherein said fresh gas supply unit comprises an anesthetic evaporator through which fresh gas flows.

19. A respiration system in accordance with claim 13, wherein fresh gas is supplied to said rebreathing line downstream of said radial compressor and upstream of said inspiratory branch nonreturn valve with respect to a flow of fluid in said rebreathing line via said fresh gas supply unit, wherein oxygen is supplied to said rebreathing line downstream of said radial compressor and upstream of said inspiratory branch nonreturn valve with respect to said flow of fluid in said rebreathing line via said oxygen flushing source.

20. A respiration system in accordance with claim 13, wherein fresh gas is delivered to said rebreathing line at a fresh gas delivery position via said fresh gas supply unit and the oxygen is delivered to said rebreathing line at an oxygen delivery position via said oxygen flushing source, said fresh gas delivery position and said oxygen delivery position being located downstream of said carbon dioxide absorber and upstream of said inspiratory branch nonreturn valve with respect to a flow of fluid in said rebreathing line.

* * * * *